United States Patent [19]

Ron et al.

[11] Patent Number: 5,688,915
[45] Date of Patent: Nov. 18, 1997

[54] LONG TERM MAINTENANCE OF LYMPHOCYTES IN VITRO

[75] Inventors: Yakov Ron, East Brunswick; Joseph Dougherty, Hampton, both of N.J.

[73] Assignee: The University of Medicine and Dentistry of New Jersey, Newark, N.J.

[21] Appl. No.: 457,482

[22] Filed: Jun. 1, 1995

[51] Int. Cl.$^6$ .................. C12N 5/00; C12N 5/08; C12Q 1/04

[52] U.S. Cl. .......... 530/380; 435/41; 435/240.1; 435/240.2; 435/240.25; 435/240.3; 435/240.31

[58] Field of Search .............. 530/380; 435/41, 435/240.1, 240.2, 240.25, 240.3, 240.31

[56] References Cited

U.S. PATENT DOCUMENTS

| | | | |
|---|---|---|---|
| 4,963,489 | 10/1990 | Naughton et al. | 435/240.1 |
| 5,124,263 | 6/1992 | Temin et al. | 435/240.2 |
| 5,188,959 | 2/1993 | Haberman | 435/240.243 |
| 5,399,346 | 3/1995 | Anderson et al. | 424/93.21 |
| 5,447,861 | 9/1995 | Collins et al. | 435/240.21 |

FOREIGN PATENT DOCUMENTS

WO 95/07358  3/1995  WIPO.

OTHER PUBLICATIONS

Kuo et al., 1993, Blood 82:845–52.
Barillari et al., 1992, J. Immunol. 149:3727–34.
Gabbianelli et al., 1990, Science 249:1561–4.
Kasid et al., 1990, Proc. Natl. Acad. Sci. USA 87:473–7.
Schulze-Osthoff et al., 1990, J. Invest. Dermatol. 95:238–40.
Ensoli et al., 1989, Science 243:223–6.
Burgess et al, 1989, Ann. Rev. Biochem. 58:575–606.
Tamir et al. (1989) Int. J. Cell Cloning 7:373–84.
Whitlock and Witte, 1982, Proc. Natl. Acad. Sci. USA 79:3608–12.
Brunner et al., 1980, J. Immunol. 124:1627–34.

*Primary Examiner*—Nathan M. Nutter
*Attorney, Agent, or Firm*—Klauber & Jackson

[57] ABSTRACT

Long term culture of resting T lymphocytes. The present invention provides methods and compositions for maintaining resting, mature T lymphocytes (cells) for long term in the absence of mitogens, antigens, or stimulatory cytokines, in which the T cells maintaining their ability to respond to nitrogens and allogenic cells. T cells cultured under such conditions can be used as target cells for retroviral vector-mediated gene transfer and implemented in certain gene therapy applications. The culturing conditions described herein allow for the continuous availability of T lymphocytes for various pharmacological, diagnostic, gene therapy, and experimental purposes, and can be utilized for any application requiring non-stimulated T lymphocytes. In specific examples, umbilical cord blood and peripheral blood T lymphocytes and endothelial-like adherent monocytes are cultured in DMEM, 2% 2-mercaptoethanol containing either 20% horse serum, or RPMI 2% 2-ME containing 10% fetal calf serum supplemented with basic fibroblast growth factor for up to three months.

10 Claims, 7 Drawing Sheets

LONG TERM MAINTENANCE OF LYMPHOCYTES IN VITRO

FIELD OF THE INVENTION

The present invention relates generally to a method of maintaining non-adherent resting, mature T lymphocytes, in which cells maintain their ability to respond to mitogens and allogeneic cells. The maintenance of these T cells is achieved without the use of stimulatory cytokines, antigens, or mitogens. T cells cultured under such culturing conditions can be used as target cells for retroviral vector-mediated gene transfer and implemented in certain gene therapy applications.

BACKGROUND OF THE INVENTION

Normal, unstimulated human peripheral T lymphocytes do not survive in vitro for long periods, e.g., longer than a few days. Generally, in vitro propagation of primary T lymphocytes involves two steps: 1) activation of the T cells with either antigen or mitogen, and 2) expansion of the activated T cells with cytokines, usually interleukin-2 (IL-2) (Brunner et al., 1980, J. Immunol. 124:1627; Kasid et al., 1990, Proc. Natl. Acad. Sci. USA 87:473). T cells that have been cultured in this manner may persist for several months in vitro. These methods are useful for generating T cell lines specific for a particular antigen, or for expanding primary T cells (Brunner et al., 1980, J. Immunol. 124:1627; Kasid et al, 1990, Proc. Natl. Acad. Sci. USA 87:473). They are not adequate, however, for culturing resting primary T cells, since these do not express high affinity IL-2 receptors. Nor are they useful for studying T cell biology independent of the effects of IL-2. A tissue culture system that does not require continuous T cell stimulation would be particularly attractive and useful for studying HIV infection of resting T lymphocytes, as well as the mechanisms leading to the initiation and maintenance of viral latency, since it more closely resembles the in vivo situation. In addition, a system in which primary T cells could be maintained in vitro, and harvested, can provide beneficial and useful means for studying T cell biology or for clinical applications such as gene therapy.

Tamir et al. (1989, Intl. J. Cell Cloning 7:373–384) reported that long-term hemopoiesis in culture is supported by stromal cell lines and clones from murine bone marrow and thymus stroma. The stromal cell lines included precursor T-cells and pre-B cells. Both bone marrow and thymus stroma induced multi-lineage hemopoiesis. The predominance of a cell type depended on the presence of cytokines, such as IL-2 or a thymic hormone, in the culture medium.

Human Immunodeficiency Virus Infection

An early and likely critical deficit during infection with HIV-1 is a loss of immunologic memory in the CD4$^+$ T helper compartment (Murray et al., 1985, New Engl. J. Med. 313:1504–1510; Lane et al., 1985, New Engl. J. Med. 313:79–84; van Noesel et al.,1994, J. Clin. Invest. 86, 293–299). There is a loss of reactivity to test antigens in vivo (delayed type hypersensitivity responses) and a loss of T cell function in culture. It is clear that HIV-1 can infect and kill CD4$^+$ T cells that are responding to antigens and superantigens (Cameron et al., 1994, Aids Res. Hum. Retroviruses 10, 61–71). However, in what sites of an infected individual is HIV-1 being generated, and why is reduced CD4$^+$ T cell memory such an early and profound occurrence?

The presence of virus in individuals infected with HIV-1 is clearly documented. In blood, infectious virus (Ho et al., 1989, N. Engl. J. Med. 321, 1621–1625; Coombs et al., 1989, N. Engl. J. Med. 321, 1626–1631), numerous viral particles (Piatak Jr. et al., 1993, Science 259, 1749–1754), and cells with HIV-1 transcripts (Saksela et al., 1994, Proc. Natl. Acad. Sci. USA 91:1104–1108) are present. These manifestations of a significant virus burden appear to increase progressively during disease. In lymphoid tissues, particularly in the germinal center regions, larger burdens of HIV-1 can be identified relative to blood (Armstrong and Horne, 1984, Lancet II., 370–372; Biberfeld et al., 1986, Am. J. Pathol. 125, 436–442; Racz et al., 1986, Prog. Allergy 37, 81–181; Spiegel et al., 1992, Am. J. Pathol. 140, 15–22; Pantaleo et al., 1993, Nature 362, 355–358; Embretson et al., 1993, Nature 362, 359–362).

According to the World Health Organization, more than 75% of new HIV infections occur during heterosexual sex; many more result from male homosexual relations. Sexual contact involves the mucous membranes in the vagina, penis, rectum, and oral cavity. To date, apart from physical barriers such as condoms, there is no effective way to prevent the spread of HIV infection, and AIDS. In particular, there is no vaccine for HIV, and the prospect of developing an HIV vaccine within the next few years are dim. Since individuals reluctantly change sexual practices, including condom use, the prospects for controlling transmission through behavior are not much better. An attractive third strategy for preventing HIV infection that has lately garnered considerable attention is application of a topical microbicide to the affected areas, e.g., skin and mucous membranes (see, e.g., Taylor, 1994, J. NIH Res. 6:26–27). Finding compounds that can block HIV-1 transmission during sex is becoming a high priority for public health officials in the U.S. and abroad (ibid). Thus, there is a clear need in the art for an assay to identify such compounds. Such an assay relies on understanding the mechanism of sexual transmission of HIV and infection of resting T cells.

The citation of any reference herein should not be construed as an admission that such reference is available as prior art to the instant invention.

SUMMARY OF THE INVENTION

The present invention relates to the development of a culturing system for the long-term maintenance of T lymphocytes in vitro, i.e., CD4 and CD8 T lymphocyte populations, without the need for exogenous stimulation with cytokines, mitogens, or antigens. The culturing conditions described herein allow for the continuous availability of resting T lymphocytes for various pharmacological, gene therapy, diagnostic, therapeutic, and experimental purposes, and can be utilized for any application requiring non-stimulated T lymphocytes for long periods of time.

Thus, in broad aspect, the invention provides a method for maintaining resting T lymphocytes in culture for longer than one week. The method comprises culturing T lymphocytes on a layer of endothelial-like adherent blood monocytes in culture medium comprising an adherent blood monocyte growth factor. According to the invention, the number of T cells after one week in culture exceeds 60% of the number at the start; moreover, after one month about 100% of the viable lymphocytes are T cells. At least about 85% of the T cells persist in culture after each successive month (the number of T cells decreasing by approximately 15% per month) following the first week.

The endothelial-like adherent blood monocytes, and the T lymphocytes, can be derived from peripheral blood or umbilical cord blood. In a specific embodiment, both types of cells are derived from the same source. It is further contemplated that resting T cell lines and clones can also be cultured on the endothelial-like adherent cells, obviating the need for culturing these cells in the presence of stimulating cytokines such as IL-2, or mitogens.

In a preferred aspect, the adherent cells and the T lymphocytes are human cells.

According to the invention, in one embodiment the adherent blood monocyte growth factor is a high concentration of serum. The high concentration of serum is greater than 15% of culture medium. In a specific embodiment, 20% horse serum is used. Alternatively, the adherent blood monocyte growth factor may be a cytokine present in an amount effective to maintain the adherent blood monocytes. In another specific embodiment, in which the growth factor is a cytokine, present in an amount effective to maintain the adherent blood monocytes the adherent blood monocyte growth factor is basic fibroblast growth factor (bFGF). The effective concentration of adherent blood monocyte growth factor, e.g., high serum content or bFGF, as well as other nutrients in the culture medium, is maintained by refeeding the cultures, for example by replacing about one-half of the medium with fresh medium every week or so.

In addition to methods, the present invention relates to compositions for the long-term culture of resting T lymphocytes. A composition of the invention comprises cell culture medium, resting T lymphocytes, and a layer of endothelial-like adherent blood monocytes, wherein the culture medium comprises an adherent blood monocyte growth factor. In specific embodiments, the endothelial-like adherent blood monocytes and the T lymphocytes are independently derived from peripheral blood or umbilical cord blood. Preferably, the cells are human.

According to the invention, the adherent blood monocyte growth factor can be a high concentration of serum, e.g., serum is greater than 15% of culture medium. In a specific embodiment, the culture medium of the composition contains 20% horse serum. In another embodiment, the growth factor may be a cytokine present in an mount effective to maintain the adherent blood monocytes. In a specific embodiment, the adherent blood monocyte growth factor is basic fibroblast growth factor.

In a preferred aspect, the culture medium is changed at least one time each week by replacing one-half of the media with fresh media without disturbing non-adherent cells. Preferably the culture medium comprises a heterogenic serum for the cells, e.g., human serum for cells from human blood.

Accordingly, the present invention provides a culture system for long-term maintenance of resting T lymphocytes. T cell growth is supported by the peripheral blood-derived adherent cell monolayer, which is comprised of endothelial-like cells. These cells have a phenotype closely resembling that of activated endothelial cells including the expression of E-selectin and HLA-DR. It is also presumed that these cells secrete growth factor(s) that can support the maintenance of mature T cells, since the T cells appear to remain in a quiescent phase for a the duration of the culture. The T cells can be harvested from the cultures and stimulated with mitogens or allogeneic cells at any point, thus remaining immunocompetent. Both $CD4^+$ and $CD8^+$ cells can persist in culture, and the proportion of each cell type will generally remain the same for the duration of the culture. Furthermore, the invention provides for harvested T cells from one to three month-old cultures to be used as target cells for retroviral vector-mediated gene transfer. This is achieved by co-cultivating harvested T cells with helper T cells which produce a retroviral vector containing a gene of interest for a 24 to 48-hour period. The efficiency of infection is similar to that obtained for fresh peripheral blood T cells (21–28%), suggesting that the long-term cultured cells of the present invention are useful, in certain cases, for somatic cell gene therapy protocols.

A primary object of the present invention is to provide a method for culturing and maintaining resting T lymphocytes in vitro, without requiring any stimulation, e.g., with stimulatory cytokines, antigens, or mitogens, for maintaining viability.

A further object of the present invention is to provide a method of long term culturing T lymphocytes in vitro, wherein said lymphocytes are mature and remain non-adherent, small, resting, and retain their ability for a primary response to mitogens and allogeneic cells during the period of culturing.

A still further object of the invention is to provide a method long term of culturing T lymphocytes in vitro wherein the ratio of $CD4^+$ and $CD8^+$ cells is maintained throughout the entire period of culturing.

A still further object of the invention is to provide a method for long term culturing T lymphocytes in vitro wherein said lymphocytes can be utilized as target cells for gene therapy.

Yet another object of the invention is to provide long term cultural T lymphocytes for screening and efficacy testing of anti-HIV drugs, drugs that block lymphocyte transformation, or any drug intended for therapies involving T lymphocytes.

Another object of the invention to provide a method of culturing T lymphocytes wherein the lymphocytes are supported by a monolayer of adherent cells comprised of endothelial-like cells derived from peripheral blood.

A further object of the invention is to provide a cell culturing system wherein endothelial-like cells are induced to form a monolayer when peripheral blood is co-cultured with fibroblast growth factor or in the presence of high concentrations of serum.

Another object of the present invention is to provide a means for testing drugs that prevent or interfere with the interactions between endothelial-like cells and T lymphocytes for use in treatment of diseases that emulate these interactions such as autoimmune diseases.

These and other objects of the invention will be made more clear by reference to the accompanying Drawings and Detailed Description of the Invention, infra.

DETAILED DESCRIPTION OF THE INVENTION

Figure 1:
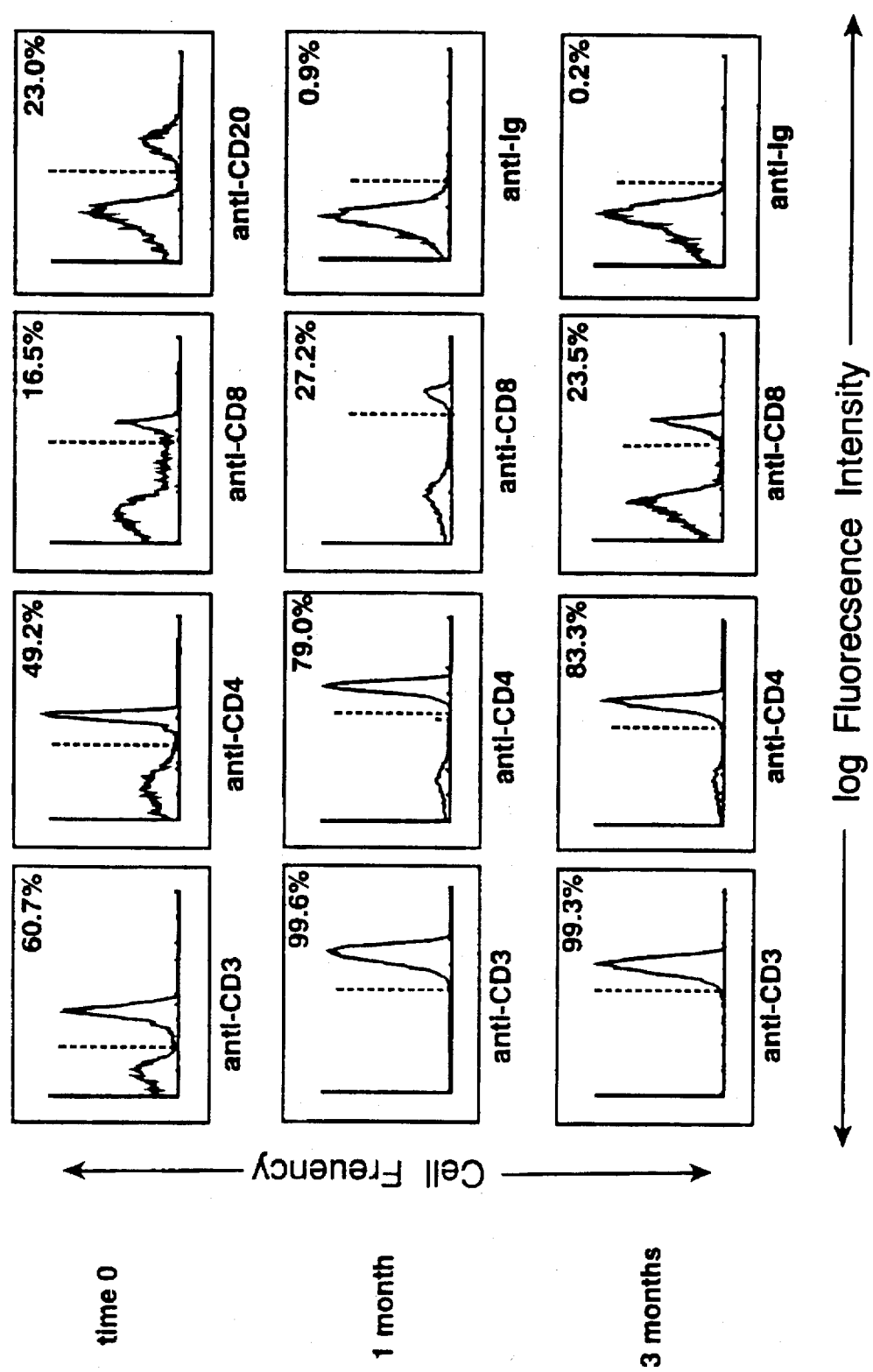
FIG. 1. Flow cytometric analyses of human umbilical cord blood cultures. Fresh human umbilical cord blood lymphocytes were isolated by density gradient separation on Hypaque ficoll. Mononuclear cells were plated for long-term culture as described in the Materials and Methods. An aliquot of fresh cells was stained with FITC-labeled monoclonal antibodies specific for human CD3, CD4, CD8, CD20, and Ig, $10^6$ cells/sample. Long-term cultured cells were harvested for staining at 1 and 3 months. 5000 cells/sample were analyzed on an Epics Profile, depicted in each histogram. The Y-axis corresponds to the relative number of cells. The X-axis represents log of the fluorescence.

The present invention pertains to a method of culturing T lymphocytes in vitro wherein T lymphocytes are cultured and maintained on a monolayer of adherent endothelial-like cells for at least one month, preferably about 3 months, and more preferably indefinitely, and wherein culturing conditions are such that use of stimulatory cytokines, antigens, or mitogens is unnecessary.

The present invention is based, in part, on development of an in vitro culture system for the long-term maintenance of primary, human peripheral blood and umbilical cord blood T lymphocytes, which does not rely on the use of stimulatory cytokines, antigens, or mitogens. In these cultures, a monolayer of adherent cells, some spindle-shaped, and some resembling macrophages, develops within a week of initiating the culture. All adherent cells were positive for the extracellular matrix proteins laminin and fibronectin, the intermediate filament vimentin, and for the surface markers MHC class II, PECAM I (CD31), and E-selectin (ELAM-1, CD62E). They were negative for the leukocyte common antigen (CD45), the macrophage marker MO-2 (CD14), muscle-specific actin, and Factor VIII-related antigen. These monolayers supported the maintenance of non-adherent, resting, mature T cells for up to 3 months, and the resting T cells retained their ability to respond to mitogens and allogeneic cells. Both CD4$^+$ and CD8$^+$ cells were maintained in the long term culture, and the proportion of CD4$^+$ and CD8$^+$ cells remained constant after 3 months in culture. The invention is further based on use of the T cells from 2 month old cultures as target cells for retroviral vector-mediated gene transfer. Up to 30% of the long-term T cells expressed the transferred lacZ gene following infection with a retroviral vector. The infection efficiency was similar to that obtained for fresh peripheral blood T cells, indicating that the long-term-cultured cells should be suitable for gene therapy applications.

In a specific embodiment, to establish and maintain a long-term T lymphocyte culture according to the invention, the cell density of the mononuclear cells prepared from human peripheral blood or umbilical cord blood should be within the range of 0.5 to $1.0 \times 10^6$ cells per ml. In a specific example, infra, the media used was DMEM supplemented with 20% horse serum and 2-mercaptoethanol, and "Dexter-like" cultures without IL-3. In another specific embodiment, the media used was RPMI media supplemented with 10% fetal calf serum, 2-mercaptoethanol, and an amount of basic fibroblast growth factor effective to maintain the viability of the adherent cells, for example, 20 ng/ml.

Once the culture is established, i.e., an adherent monolayer of endothelial-like cells forms with a non-adherent layer of T lymphocytes residing thereon, it can be maintained under the conditions described herein for periods of at least up to three months. Although not intending to be limited by any particular theory concerning the basis of the present invention, it is believed that the growth and maintenance of T lymphocytes on the monolayer is a result of a growth factor or factors secreted by the adherent cells, thus obviating the need for the addition of such factors, including stimulatory cytokines, antigens or mitogens, under the conditions of the present invention.

Within two weeks of initiating the culture, a semi-confluent lawn of adherent, stromal-like cells forms. The lymphocyte population comprising CD4$^+$ and CD8$^+$ cells forms a non-adherent layer residing on the stromal-like cells. Both of the cell types can remain in culture for at least up to three months if they are maintained according to the conditions of the invention. Other cell types do exist initially in the culture, such as B cells, but these do not persist.

The present invention provides a high yield, extremely efficient method for maintaining resting T cells. Generally, 60% of the T lymphocytes added at the beginning of the cultures can be harvested at the end of three months. Yields were found to decrease by only about 15% per month after inception of the culture. The ratio of CD4$^+$ to CD8$^+$ remains stable during the culture, in contrast to culture methods that involve stimulatory agents such as IL-2. The unstimulated T cells maintain the morphology of small resting T cells, and respond normally to mitogenic an antigenic (allogeneic) stimulation. The present invention requires only 10 ml of peripheral blood to obtain the endothelial-like adherent blood cells needed to maintain $5 \times 10^6$ T lymphocytes for three months.

Longer term T cell cultures can be propagated by seeding the T cells on fresh endothelial-like adherent blood monocytes. Preferably, the adherent cells used to support already established long-term T cells are first depleted of endogenous T cells, e.g., by panning, nylon wool purification, complement mediated lysis, or some similar means.

Various terms are used throughout this specification, which have the meanings set forth below:

As used herein, the term "T lymphocyte," or its alternative, "T cell," refers to a differentiated lymphocyte with a phenotype $CD3^+$, T cell receptor (TcR)-positive (either $\alpha\beta$, or $\gamma,\delta$), and either $CD4^+$ or $CD8^+$. Preferably, the T lymphocytes are derived from peripheral blood or umbilical cord blood, although the invention contemplates that T cell lines and clones can be cultured on the adherent blood monocytes.

According to the invention, the resting T cells conserve the functional activity of primary T cells. As used herein, the term "functional activity" and the like relates to the changes in the phenotype, morphology, cytokine production, and other characteristics and properties of T cells. One functional activity of T cells is the ability to proliferate in response to mitogen or antigen. Another T cell functional activity is the secretion of cytokines such as IL-2, IL-4, and the like.

The term "endothelial-like adherent blood monocyte" or "adherent blood monocyte" is used herein to refer to the stromal cells that form an adherent monolayer in the cell cultures that is critical to the long-term maintenance of the T lymphocytes. The adherent cell population of the invention is composed of endothelial-like cells with varied morphology: about half the cells with a spindle-shaped morphology, and the other half with a macrophage like morphology. The phenotype of the supportive adherent cell layer is characterized immunohistochemically as staining positive for fibronectin, laminin, vimentin, anti-E-selectin (ELAM-1, CD62E), HLA DR antigens, PECAM-1 (platelet-endothelial cell adhesion molecule-1, CD31; negative for Factor VIII-related antigen, muscle-specific actin, the leukocyte common antigen (CD45) or the macrophage marker MO-2 (CD14). From their morphology and phenotype, the cells are suitably described as endothelial-like.

The term "adherent blood cell growth factor" is used herein to refer to a protein, e.g., a cytokine, or a complex mixture of factors, e.g., serum, that maintains the viability of the adherent blood monocytes, and promotes their ability to support the T lymphocytes in culture. For example, the growth factor can be a high serum content in the culture medium, e.g., greater than 15% serum. In a specific embodiment, 20% horse serum provides growth factor activity. In another embodiment, the growth factor is basic fibroblast growth factor, e.g., at 20 ng/ml.

As used herein, the term culture refers to the in vitro maintenance of cells. Generally, the cells are cultured in culture medium, which is a nutrient-rich buffered aqueous solution capable of sustaining cell growth. Various culture media suitable for the culturing of lymphocytes can be used in the practice of the invention. In specific embodiments, Dulbecco's Minimal Essential Medium (DMEM) or RPMI (frequently used T cell cultures) is used. The media are generally supplemented with 2-mercaptoethanol, e.g., 50 µM 2-ME, and contain sera, e.g., horse serum, fetal calf serum (FCS), human serum, and the like. Cell cultures are maintained in a $CO_2$ atmosphere, e.g., 5% to 12%, to maintain pH of the culture fluid, and incubated at 37° C. in a humid atmosphere. The choice of serum and the partial pressure of $CO_2$ in the incubator are considerations in the choice of culture medium.

As used herein, the term "cytokine" used in reference to T lymphocyte stimulation generally refers to interleukin-2 (IL-2), but includes other T cell stimulatory cytokines, such as but not limited to interleukin-4 (IL-4). The term "mitogen" is used herein to refer to a non-specific stimulator of T cell activation, e.g., phytohemagglutinin (PHA), phorbol myristate acetate (PMA), or concanavalin A (Con A).

Evaluation of T Cell Functional Activity and Diagnosis

Using techniques that are well known in the art, T lymphocyte activation, e.g., proliferative responses, can be measured in vitro. In a specific embodiment, infra, T cell responses are detected by measuring incorporation of $^3$H-thymidine, which increases with DNA synthesis associated with proliferation. Cell proliferation can also be detected using an MTT assay (Mossman, 1983, J. Immunol. Methods 65:55–63; Niks and Otto, 1990, J. Immunol. Methods 130:140–151). Stimulation can be determined by increased expression of cellular markers on the T cells, such as interleukin 2 receptor, LFA-3, etc. Similarly, lymphokine production assays can indicate T cell proliferation. Generally, production of lymphokines is detected immunologically, most frequently by ELISA. However, lymphokine production can be assayed using co-stimulation assays (see, e.g., Birkeland et al., 1987, J. Exp. Med. 166:506 [IL-4 assay]; Fehlner et al., 1991, J. Immunol. 146:799–806 [CTLL co-stimulation assay for IL-2]; Mossmann et al., 1986, J. Immunol. 136:2348) or using the ELISPOT technique (Czerkinsky, et al., 1988, J. Immunol. Methods 110:29). Alternatively, mRNA for lymphokines can be detected, e.g., by amplification (see Brenner, et al., 1989, Biotechniques 7:1096) or in situ hybridization (see, e.g., Kasaian and Biron, 1989, J. Immunol. 142:1287).

The present invention advantageously provides for the long term evaluation of T lymphocytes in vitro under resting conditions. Thus, the long term cultures can be used to screen or test the efficacy of anti-HIV drugs (as explained in detail, infra), to screen or test for drugs that block lymphocyte transformation, or for evaluating any drug intended for therapies involving T lymphocytes, including but not limited to immunosuppressive drugs, immunostimulatory drugs, and specific targeting agents, particularly agents to be targeted to resting T lymphocytes.

The long term cultures of the invention provide an advantageous system for evaluating T cell-endothelial interactions, which may be important for developing treatments for autoimmune disease. Likewise, the cultures of the invention provide a valuable resource for studying the role of adhesion molecules and specific recognition features involved in binding of T cells to endothelial cells.

Detection of the Presence of HIV Infected Cells

The method of the invention specifically related to identification of agents that can inhibit or prevent HIV infection of T cells, e.g., transfer of HIV to memory T cells, relies on detecting the presence and productivity of HIV infection. HIV isolates can be obtained from the NIH AIDS Research and Reference Reagent Program, operated by Ogden Bio-Services Corporation, 684 Lofstrand Lane, Rockville, Md. 20850. Primary HIV isolates are also available from HIV-positive individuals and people with AIDS. Alternatively, cells infected with HIV, rather than free isolates, can be used to infect assay cultures of the invention.

HIV can be detected in cells by many techniques, including the presence of HIV mRNA or DNA, the presence of HIV antigens in cells or in the culture fluid, and the presence of HIV virions themselves. Many of these techniques also provide for determining the productivity of an HIV infection, which is a measure of activity and virulence.

The presence of HIV mRNA or integrated DNA is preferably detected using polymerase chain reaction (PCR) (Cameron et al., 1992, Science 257:383–387; Saksela et al., 1994, Proc. Natl. Acad. Sci. USA 91:1104–1108). For example, HIV mRNA can be detected by reverse transcriptase-initiated PCR (see, e.g., Saksela et al., 1993, J. Virol. 67:7423–27). PCR can be carried out, e.g., by use of a Perkin-Elmer Cetus thermal cycler and Taq polymerase (Gene Amp™, Boehringer Mannheim). The amplified PCR products can be detected by incorporation of radiolabeled nucleotides, endlabeling, e.g., with $\gamma^{32}$P-ATP, or by staining with ethidium bromide. However, according to the present invention, radiolabels are preferred as these can yield more quantitative information, e.g., by analysis of band density after gel electrophoresis and autoradiography. Virus (provirus) copy number can be determined by comparison of the intensity of the PCR band with a standard, such as the latently infected cell line ACH-2, contains one copy of provirus in each cell (Folks et al., 1986, Science 231:600–602). In a specific embodiment, PCR of the vital gag sequence can be used. Both the presence of HIV and its level of activity can be determined by analysis of mRNA. For quantitation of the level of HIV mRNA, after gel electrophoresis and autoradiography, the intensities of mRNA signals can be compared with those of the control RNAs analyzed in parallel to estimate the approximate amounts of HIV-specific mRNAs present in the samples. The amount of viral mRNA corresponds to the level of viral activity (see, e.g., Saksela et al., 1994, supra).

Alternatively, the presence of HIV can be determined by an assay for reverse transcriptase. Reverse transcriptase can be detected immunologically, using an antibody to the enzyme. Preferably, reverse transcriptase is detected using an enzyme activity assay, e.g., as described in Cameron et al. (1992, supra).

HIV infection of cells and the productivity of infection can also be detected by detecting the presence of HIV antigens, i.e., HIV proteins (including reverse transcriptase). In a specific embodiment, the presence of p24 antigen can be indicative of infection with HIV. p24 antigen can be detected immunologically, e.g., at the single cell level with the monoclonal antibody produced by hybridoma 183, clone H12-5C (Chesebro et al., 1992, J. Virol. 66:6547–6554), or in the culture fluid using a p24 detection kit (e.g., New England Nuclear kit #NEK-060S).

In another embodiment, the presence and quantity of HIV can be detected by electron microscopy. In particular, viral buds can be observed on the surface of infected cells, and free in proximity to infected cells.

In yet another embodiment, productive HIV infection can be detected by the presence of T lymphocyte syncytia. Syncytia can be detected under light microscopy, by immunostaining for the presence of T lymphocyte markers on the syncytia.

Various drugs can be tested for their effectiveness against HIV, or for other purposes in modifying T cell functional activity, using the parameters set forth above. Although not intending to be limited to any particular agent or mode of operation, the present invention contemplates testing of a number of agents, including, but not limited to, cytokines, non-steroidal anti-inflammatory agents, steroids, antiviral compounds (nucleotide analog-type inhibitors of the reverse transcriptase, such as but not limited to AZT (zidovudine, Retrovir), 2', 3'-dideoxy-inosine (ddI, Videx), 2', 3-dideoxycytidine (ddC, zalcitabine, HIVID), 3TC (Lamivadine), d4T (Stavudine), FLT, and PMEA; non-nucleotide analog inhibitors of reverse transcriptase, such as Nevirapine (BI-RG-587), TIBO (R82913), pyrinodes (such as R-697,661 and L-696,227), bis(heteroary)piperazines (BHAPs, such as U-87201E and U-90,152), atevirdine mesylate (ATV) and R-89431; HIV protease inhibitors, include substrate analogs and non-analogs, such as Ro 31-8959, A-77003 and A-80987; HIV Tat protein inhibitors, such as Ro 5-3335 and Ro 27-7429; blockers of viral entry into cells, such as soluble CD4 protein (sCD4), and chimeric sCD4 derivatives, such as CD4-IgG and CD4-PE40; blockers of HIV RNaseH activity, such as the AZT derivative azidothymidine monophosphate; drugs that alter the intracellular milieu to create conditions less favorable for viral replication, such as the free-radical scavengers and glutathione-level restoring drugs (N-acetylcysteine and similar drugs), and thalidomine (which seems to lower blood TNF-$\alpha$ levels)), antibiotics (such as gramicidin), analogs or inhibitors of leukocyte adhesion molecules (e.g., CD80 and CD54), antibodies to leukocyte adhesion molecules, oligosaccharides, polysaccharides, glycosaminoglycans (e.g., hyauronic acid, chitosan, pentosan polysulfate, aginate, and the carbohydrate portions of the proteoglycans heparin, keratan sulfate, chondroitin sulfate, heparan sulfate, dermatan sulfate, and the like), proteoglycans, charged high molecular weight carbohydrates (e.g., dextran sulfate), to mention but a few, can be assayed according to the methods of the present invention.

Gene Therapy With Long-Term Cultured T Cells

According to the invention, the long term cultured T cells provide an ideal source of cells for transfection and reintroduction in vivo for gene therapy. Various protocols known in the art can be employed for transfecting the long-term cultured T lymphocytes for gene therapy, such as the procedures described in U.S. Pat. No. 5,399,346, issued Mar. 21, 1995 to Anderson et al.; Mann et al., 1983, Cell 33:153; Temin et al., U.S. Pat. No. 4,650,764; Temin et al., U.S. Pat. No. 4,980,289; Markowitz et al., 1988, J. Virol. 62:1120; Temin et al., U.S. Pat. No. 5,124,263; and the preferred procedures described in copending U.S. patent application Ser. No. 08/302,23J by Dougherty et al., and International Patent Publication WO 95/07358, Mar. 16, 1995, by Dougherty et al. Many of the producer cell line-vector combinations known in the art can be used to practice the instant invention. Generally, a vector is transfected into a helper cell line. Cell lines that produce about $5\times10^5$ c.f.u./ml are selected. Subcloning of these cell will yield a line that is capable of producing up to $10^7$ c.f.u./ml of virus. In a specific embodiment for gene transfer into murine lymphoid cells, the cell line is the GP+E-86 cell line (Elwood et al., 1994, Leukemia 8:106–114; Matsushita et al., 1993, Thrombosis Res. 69:387–393; Wilson et al., 1993, Human Gene Therapy 4:25–34; Markowitz et al., 1990, Ann. N.Y. Acad. Sci. 612:407–414; Moore et al., 1990, Blood 75:2085–92), which is a NIH 3T3-based cell line, and the vector is selected from the group consisting of pN2 (Moore et al., 1991, Human Gene Therapy, 2:307–315; Alford and Belmont, 1990, Human Gene Therapy 1:269–276; Stoeckert et al., 1990, Experimental Hematology 18:1164–1170) and pAsADA, which are Maloney murine leukemia virus-based retroviral vectors that contain the neo gene under control of the MLV long terminal repeat promoter. In a specific embodiment, the vector encodes the human adenosine deaminase (ADA) gene under control of the endogenous promoter. In another specific embodiment, for gene transfer into human lymphoid cells, the vector may be pMFG-NB (Ferry et al., Proc. Natl. Acad. Sci. USA 88:8377–81), and the helper cell may be prepared from the canine osteosarcoma cell line D17, which is available from the American Type Culture Collection (ATCC), accession number CCL183. The canine cell line can be prepared as a helper line according to known techniques (e.g., Pear et at., 1993, Proc. Natl. Acad. Sci. USA 90:8392–96; Miller et al., 1991, J. Virol. 65:2220–2224; Markowitz et al., 1988, Virol. 167:400–406; Markowitz et al., 1988, J. Virol. 62:1120–24; Danos and Mulligan, 1988, Proc. Natl. Acad. Sci. USA 85:6460–64; Dougherty et al., 1989, J. Virol. 63:3209, and U.S. Pat. No. 4,980,289 and U.S. Pat. No. 5,124,263 to Temin and Dougherty). In addition, retroviral gene transfer involves an infection protocol. Appropriate growth factors are added to the T lymphocytes to be infected to keep induce cell proliferation. For T cells, sequential treatment with PHA or concanavalin A and interleukin-2 may be used. Preferably, the T lymphocytes are stimulated for the length of time necessary to induce proliferation, e.g., about 24 hours. The stimulated lymphocytes are then co-cultivated with a lawn of helper (producer) cells, having a very high virus titer, in the presence of the growth factors. Preferably, the helper cells are irradiated. Irradiation stops the helper/producer cells from growing but still enables the cells to produce virus. Thus, the confluent lawn of producer cells does not overgrow the plate and lift off. The producer cells adhere to the plate and the lymphocytes do not. As the lymphocytes proliferate, a necessary step for virus integration, the lymphocytes become infected with the transgenic virus. The infected (or transfected) cells are then harvested for administration to a subject.

Alternatively, attenuated or defective DNA virus, such as but not limited to herpes simplex virus (HSV), papillomavirus, Epstein Barr virus (EBV), adenovirus, adeno-associated virus (AAV), and the like can be used for the gene transfer. Defective viruses, which entirely or almost entirely lack viral genes, are preferred. Defective virus is not infective after introduction into a cell. Examples of particular vectors include, but are not limited to, a defective herpes virus 1 (HSV1) vector (Kaplitt et al., 1991, Molec. Cell. Neurosci. 2:320–330), an attenuated adenovirus vector, such as the vector described by Stratford-Perricaudet et al. (1992, J. Clin. Invest. 90:626–630), and a defective adeno-associated virus vector (Samulski et al., 1987, J. Virol. 61:3096–3101; Samulski et al., 1989, J. Virol. 63:3822–3828).

In another embodiment, the vector can be introduced by lipofection. For the past decade, there has been increasing use of liposomes for encapsulation and transfection of nucleic acids in vitro. Synthetic cationic lipids designed to limit the difficulties and dangers encountered with liposome mediated transfection can be used to prepare liposomes for transfection of a gene (Felgner, et. al., 1987, Proc. Natl. Acad. Sci. U.S.A. 84:7413–7417; see Mackey, et al., 1988, Proc. Natl. Acad. Sci. U.S.A. 85:8027–8031)). The use of cationic lipids may promote encapsulation of negatively charged nucleic acids, and also promote fusion with negatively charged cell membranes (Felgner and Ringold, 1989, Science 337:387–388). Lipids may be chemically coupled to other molecules for the purpose of targeting (see Mackey, et. al., 1988, supra). Targeted peptides, e.g., hormones or neurotransmitters, and proteins such as antibodies, or non-peptide molecules could be coupled to liposomes chemically.

It is also possible to introduce the vector in vitro as a naked DNA plasmid. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun, or use of a DNA vector transporter (see, e.g., WU et al., 1992, J. Biol. Chem. 267:963–967; Wu and Wu, 1988, J. Biol. Chem. 263:14621–14624; Hartmut et al., Canadian Patent Application No. 2,012,311, filed Mar. 15, 1990).

The gene transfer allows for the potential correction of genetic disorders originating from genetic defects in T lymphocytes and also for the correction of other genetic disorders in which a missing gene product may be supplied systemically by lymphocytes. In a specific embodiment, the human adenosine deaminase (ADA) gene can be introduced into the T lymphocytes. Other genes of interest for introduction include CD43 (mutation of this protein leads to Wiskoff-Aldrich syndrome), CD40 ligand (gp39, mutations of which lead to X-linked hyper IgM syndrome), or for supplying soluble gene products, such as Factor VIII or Factor IX.

Therapeutic Methods and Compositions

In one embodiment, the T cells maintained in long-term culture in vitro can be administered to a subject in need of mature T lymphocytes, e.g., an individual who is immunosuppressed. Such individuals include, but are not limited to, subjects who have undergone organ transplantation (provided organ rejection by the in vitro cultured T cells can be prevented), bone marrow transplantation after ablation of bone marrow by chemotherapy or radiation, the aged, individuals suffering from viral infections such as Epstein-Barr virus, and the like. If possible, autologous T lymphocytes can be removed prior to a procedure or onset of a condition that will result in immunosuppression, and maintained in culture without the need for exogenous stimulation until required to be re-administered to the subject.

For example, T cells from a line or clone specific for a pathogen present in an immunodeficient subject can be cultured. These T cells can then be introduced into a subject suffering from a particular illness caused by the pathogen. For example, T cells specific for an opportunistic pathogen such as toxoplasmosa, *Candida albicans*, or *Pneumocystic carnii*, can be reinfused into an immunocompromised subject suffering from infection with one of these pathogens. Administration of resting (as opposed to activated) cultural T cells may provide a more natural and effective immune response.

According to the invention, T cell activity modulating agents that may be identified through the methods disclosed herein can be prepared as pharmaceutical compositions for administration to an individual believed to be in need of such treatment. For example, an agent that inhibits T cell activation may be effective as a treatment for autoimmune disease, or for preventing organ rejection. An agent that inhibits formation of endothelial cell-T lymphocyte conjugates may block immune responses. Drugs effective against HIV may prove useful in vivo.

Accordingly, the invention provides suitable pharmaceutical compositions for use in the treatment of an immunological disease or disorder, or infection with HIV. A composition comprising "A" (where "A" is a single molecule, such as a protein) is substantially free of "B" (where "B" comprises one or more contaminating proteins, or other contaminants, but not including racemic forms of A) when at least about 75% by weight of the composition is "A". Preferably, "A" comprises at least about 90% by weight of the A+B species in the composition, most preferably at least about 99% by weight. It is also preferred that a composition, which is substantially free of contamination, contain only a single molecular weight species of each of the defined components having the activity or characteristic of interest.

Preferably, such compositions comprise the modulating agent and a pharmaceutically acceptable carrier or excipient. The phrase "pharmaceutically acceptable" refers to molecular entities and compositions that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The agent should be administered in a therapeutically effective amount to the subject in need of treatment. The phrase "therapeutically effective amount" is used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition in the host.

Evaluation of Endothelial-Like Adherent Cells

In addition to the uses of the invention drawn T lymphocytes, the present invention provides a unique culture system in terms of the adherent blood monocytes as well. Such cells evidence characteristics of Kaposis sarcoma (KS) cells. Thus, the adherent cells, e.g., available after harvesting lymphocytes, can be tested for responses to various agents to evaluate their effectiveness against KS cells. In addition, the effects of these agents on the interaction between the adherent cells and T cells can be evaluated. Ultimately, the invention provides a model for evaluating interactions between T cells and KS cells.

The present invention may be better understood by reference to the following non-limiting Examples, which are provided as exemplary of the invention.

EXAMPLE

A PERIPHERAL BLOOD DERIVED MONOLAYER SUPPORTS LONG TERM CULTURES OF T LYMPHOCYTES

The present Example demonstrates an in vitro culture system developed for the long-term maintenance of primary peripheral blood and umbilical cord blood T lymphocytes, which system does not rely on the use of stimulatory cytokines, antigen or mitogens. Instead, T cells were supported by a peripheral blood-derived monolayer of endothelial-like cells. Resting, mature T cells could be maintained for up to 3 months, remaining fully immunocompetent. Both CD4$^+$ and CD8$^+$ cells were supported. The proportion of CD4$^+$ and CD8$^+$ cells remained unchanged after 3 months in culture. T cells could be harvested from the culture at any point and stimulated with mitogens or allogeneic cells. T cells from 2 month old cultures were used as target cells for retroviral vector-mediated gene transfer. Up to 30% of the long-term T cells expressed the transferred lacZ gene following infection with a retroviral vector. The infection efficiency was similar to that obtained for fresh peripheral blood T cells, indicating that the long-term-cultured cells are suitable for certain gene therapy applications.

The supportive monolayer formed in the long-term cultures were composed of adherence cells with varied morphology: some spindle-shaped, others resembling macrophages. However, all cells had an identical cell surface phenotype as determined by staining with a panel of monoclonal antibodies. All adherent cells were positive for the extracellular matrix proteins laminin and fibronectin, the intermediate filament vimentin, and for the surface markers MHC class II, and PECAM I (CD31). The cells were negative for leukocyte common antigen (CD45, the macrophage marker MO-2 (CD14), muscle-specific actin, and Factor VIII-related antigen.

Materials and Methods

Preparation of long-term T cell cultures.

Mononuclear cells were prepared from human peripheral blood or umbilical cord blood by density separation on Hypaque ficoil (Sigma, St. Louis, Mo.). The entire mononuclear cell fraction was resuspended at a cell density of $0.5 \times 10^6$ cells/ml in either DMEM media supplemented with 20% horse serum (GIBCO, Grand Island, N.Y.), 2-mercaptoethanol (50 µM) (Sigma), and Dexter "like" cultures without IL-3 (Dexter et al., 1984, Kroc. Foundation. Series 18:57), or RPMI media supplemented with 10% fetal calf serum (GIBCO), 50 µM 2-mercaptoethanol (Whitlock and Witte, 1982, Proc. Natl. Acad. Sci. USA 79:3608), and basic fibroblast growth factor (bFGF) 20 ng/ml (PeproTech, Rocky Hill, N.J.). Cells were plated in T25 tissue culture flasks 5 ml/flask, then incubated at 37° C. with 5% CO$_2$. The media was changed once a week by pipetting and replacing one-half of the media with fresh media, being careful not to disturb the non-adherent cells. Within the first week an adherent cell layer began to form, becoming semi-confluent with time, and nonadherent cells resided on top of this layer. Periodically, the non-adherent cells were removed for counting, then returned to the cultures.

Using the procedure just described the long-term cultures from over 10 individuals ranging from newborns to 45 year old, from males and females, have been established.

Flow cytometric analysis.

Human peripheral blood and umbilical cord blood lymphocytes were analyzed at the time of culture initiation, and non-adherent cells from the long-term cultures were harvested for flow cytometry 1 month and 3 months later. T cells were stained with fluorescein-labeled monoclonal antibodies specific for human CD3 (OKT3), CD4 (OKT4), and CD8 (OKT8) (Ortho, Raritan, N.J.). Phycoerythrin-labeled B 1 (anti-CD20, Coulter, Hialeah, Fla.), and fluorescein-labeled mouse anti-human Ig (Jackson ImmunoReseach, West Grove, Pa.) were used to stain B cells. Five thousand cells, per analysis were analyzed on an Epics Profile (Coulter). Flow cytometric analysis were performed at these time points on lymphocytes harvested from four different cultures, with very similar results.

Flow cytometric analysis of newly synthesized DNA.

Nonadherent T cells were removed from long-term cultures every 2 weeks for 10 weeks and analyzed for newly synthesized DNA as a measure for cell proliferation. Cells were incubated in medium containing 10 µM of BrdU (Sigma) for 30 minutes, washed and fixed with 70% ice cold ethanol (cells can be stored for several weeks at r.t. or 4° C. weeks at this stage). Cells were resuspended in 2N HCl containing 0.5% Triton X-100 for 30 minutes at room temp. The cells were than washed 3X with borate buffer, pH 8.2, and 20 µl of FITC-mouse anti-BrdU antibodies (Beckton Dickinson). Propidium iodide (10 µM) was added just before analysis on the FACS. Newly synthesized DNA stains brightly with the anti-BrdU antibodies.

Mitomycin C-treated cells (25 µg/ml) were used as a control for cells undergoing no DNA synthesis, and Con A-pulsed cells were used as positive controls. To test the sensitivity of this system, long-term T cells were pulsed with 4 µg/ml Con A for 2 hours for stimulation.

Immunoperoxidase staining of adherent cells.

Adherent cells from the long-term cultures were fixed in 8-well chamber slides with 4% paraformaldehyde in 0.2M 100 NaPO$_4$ buffer for 15 min at 4° C., and one wash with PBS containing 0.1% Triton-x. All remaining steps were preceded by three 10 min washes with PBS at 4° C. Fixed cells were reacted with periodic acid (0.03M) to remove intrinsic peroxidase activity, then aldehyde groups were reduced with NaBH$_4$ in PBS (0.5% w/v) for 1 h. Cells were blocked with 5% BSA, then reacted sequentially, each for 30 min, with the respective primary antibody, followed by biotinylated rabbit anti-mouse or swine anti-rabbit antibody (Dakopatts, Carpinteria, Calif.), then streptavidin-peroxidase (Dakopatts). Subsequently, cells were reacted with diaminobenzidine-HCl (Dakopatts) in 3% H$_2$O$_2$ in TRIS buffer (0.05M, pH 7.72) for 20 min. Optimal antibody staining dilutions were determined by serial titration. The antibodies employed for immunohisto chemistry were leukocyte common antigen, Factor VIII-related antigen, anti-CD31, muscle-specific actin, vimentin (Dakopatts); laminin, fibronectin (Tellos, Calif.); anti-HLA-DR (Becton Dickinson, San Jose, Calif.); I3 and MO-2 (Coulter). Two different mouse anti-human E-selectin antibodies, 3B7 and 12F9.C2 were used (Erbe et al., 1992, J. Cell Biology 118:215). Mouse ascites fluid was used as negative control.

Adherent cells from long-term cultures of three different individuals were evaluated. Each antibody was tested on at least 2 individuals, except for the mouse anti-human E-Selectin which was tested on cells of only one individual. In each case, 2–4 different slides were stained with the same antibody.

T cell proliferation assay.

Fresh peripheral blood mononuclear cells and non-adherent cells from long-term cultures harvested after 1 or 3 months were plated in triplicates in half-area 96-well plates, 50,000 cells/well, at 37° C., in RPMI media supplemented with 10% fetal calf serum, and 2-mercaptoethanol (50 µM), with or without phytohemagglutinin (PHA, 4 µg/ml, Sigma). Forty- eight hours later cells were pulsed for 8 h with [$^3$H]-thymidine (1 µCi/well). Cells were harvested and analyzed for [$^3$H]-thymidine incorporation in a scintillation counter. To assess the baseline proliferation index of unstimulated cells, T cells were harvested from the cultures every 2 weeks, for 10 weeks, and plated at a concentration of 70,000 cells per half area well with 0.5 µCi of [$^3$H]-thymidine for 12 hours. As a negative control, the same number of cells were first treated with 25 µg/ml of mitomycin C (Sigma) for 1 hour at 37° C., in RPMI and then washed 3 times with PBS. In some experiments, Concanavalin A (Con A, Pharmacia) was also added to mitomycin C-treated and untreated cells to control for the effect of mitomycin C. No proliferation was observed in these cultures.

Retrovirus vector and virus-producing cells.

The MFG-NB retrovirus vector is a Moloney murine leukemia virus (MLV)-based vector containing the lacZ gene fused to an SV40 nuclear localization signal sequence, expressed from the viral LTR (Ferry et al., 1991, Proc. Natl. Acad. Sci. USA 88:8377). The vector was packaged using a cell line producing vector virus comprised mostly of MLV proteins except for the envelope glycoproteins which were derived from gibbon ape leukemia virus (GaLV). This cell line, MMG, was made by transfecting the canine osteosarcoma D17 cell line with each of the following plasmid DNAs: 1) pMFG-NB, 2) pgag-pol (Markowitz et al., 1988, J. Virol. 62:1120), 3) pGaLVenv (Wilson et al., 1989, J. Virol. 63:2374) followed by selection with G418 (0.35mg/ml), GPT (xanthine 0.25 mg/ml, mycophenolic acid 25 µg/ml, and hypoxanthine 15 µg/ml), and hygromycin (1.0 µg/ml). Cells were subcloned, and an individual line yielding vector virus stocks of 2.0×10$^7$ focus-forming units per ml was used for all experiments. The titer was quantitated by inoculation of D17 cells with serial dilutions of helper cell supernatant. Inoculated cells were stained with X-gal 2d, as previously described (Dannenberg et al., 1981, "Histochemical stains for macrophages in cell smear and tissue sections: β-galactosidase, acid phosphatase, non-specific esterse, succinic dehydrogenase, and cytochrome oxidase", *Methods For Studying Mononuclear Phagocytes*, Adams et al., eds., (New York, N.Y.: Academic Press), pp. 375) and foci consisting of 4–16 blue cells were counted. The producer cells were periodically tested and always found to be free of replication-competent virus. Screening for replication-competent virus was performed by assaying for reverse transcriptase activity after a two week D 17 amplification step (Anderson et al., 1993, Hum. Gene Ther. 4:311). The helper rescue assay (Anderson et al., 1993, Hum. Gene Ther. 4:311) was also performed after D17 amplification, using an indicator cell line consisting of D17 cells that were transfected with the defective vector BAG (Anderson et al., 1993, Hum. Gene Ther. 4:311) containing the lacZ gene and the neo gene, and maintained under selection with G418. The BAG-transfected cell line cannot produce vector virus since it lacks the viral trans sequences. If replication-competent virus were present, it would be detected by X-gal staining, or G418 selection.

Exogenous gene transfer.

Fresh peripheral blood mononuclear cells or T cells harvested from 2-month old cultures were stimulated overnight with phytohemagglutinin (4 µg/ml) in DMEM media containing 20% horse serum and 2-mercaptoethanol (50 µM). Stimulated cells were washed with PBS and resuspended at a density of 1×10$^6$ cells/ml in media containing recombinant IL-2 (10 ng/ml, PeproTech) and polybrene (6 µg/ml, Sigma), then cocultivated on confluent lawns of irradiated (1600 rad) MFG-NB vector-virus-producing cells, for 24 h at 37° C. 48 h after cocultivation, the target cells and mock-infected cells (cells cocultivated with helper cells not secreting the vector) were stained with X-gal as described (Dannenberg et al., 1981, "Histochemical stains for macrophages in cell smear and tissue sections: β-galactosidase, acid phosphatase, non-specific esterse, succinic dehydrogenase, and cytochrome oxidase", *Methods For Studying Mononuclear Phagocytes*, Adams et al., eds., (New York, N.Y.: Academic Press), pp. 375) and blue cells were scored under light microscopy. Retroviral-mediated transfer of the lacZ gene was done twice.

Results

Long-term culture of peripheral blood and umbilical cord blood mononuclear cells results in the formation of an adherent cell layer of stromal-like cells and a non-adherent cell population consisting exclusively of T cells.

Both human peripheral blood and umbilical cord blood have been reported to contain hematopoietic, pluripotential stem cells (Broxmeyer et al., 1989, Proc. Natl. Acad. Sci. USA 86:3828; Gabbianelli et al., 1990, Science 249:1561; Sekhsaria and Malech, 1993, Blood 81:2125; Yeoman et al., 1993, Proc. Natl. Acad. Sci. USA 90:10778). In an attempt to culture these hematopoietic precursor cells, we applied modified Whitlock-Witte (Whirlock and Witte, 1982, Proc. Natl. Acad. Sci. USA 79:3608) and Dexter culture conditions (Dexter et al., 1984, Kroc. Foundation. Series 18:57), which have been shown to propagate murine pre-B cells and macrophages, respectively, from long-term bone marrow cultures. Because basic fibroblast growth factor (bFGF) has been reported to increase the yield of hematopoietic progenitors isolated from human peripheral blood by inducing their response to multilineage hematopoietins (Gabbianelli et al., 1990, Science 249:1561), 20–50 ng/ml bFGF was added to some of the cultures. Both peripheral blood and cord blood mononuclear cells, when cultured under Dexter-like conditions with or without bFGF, and under the Whitlock-Witte-like conditions with bFGF, began to form a semi-confluent lawn of adherent, stromal-like cells within 2 weeks, upon which resided non-adherent cells with lymphocyte morphology. Both cell types remained in culture for up to 3 months. Upon cell typing, the putative lymphocyte population was found to consist exclusively of $CD3^+$ T cells.

Further analysis determined that both $CD4^+$ and $CD8^+$ cells were present in the culture. No B cells were detected. FIG. 1 depicts flow cytometric data of a representative cord blood lymphocyte (CBL) culture at the time of culture initiation and after 1 month and 3 months in vitro. $CD3^+$ T cells comprised 60.7% of the CBL at initiation and virtually all of the cells after 1 and 3 months. $Ig^+$ B cells initially comprised 23% of the CBL, and after 1 month no B cells could be detected. Normal ratios of $CD4^+$ and $CD8^+$ T cells were found at both time points.

Figure 2:
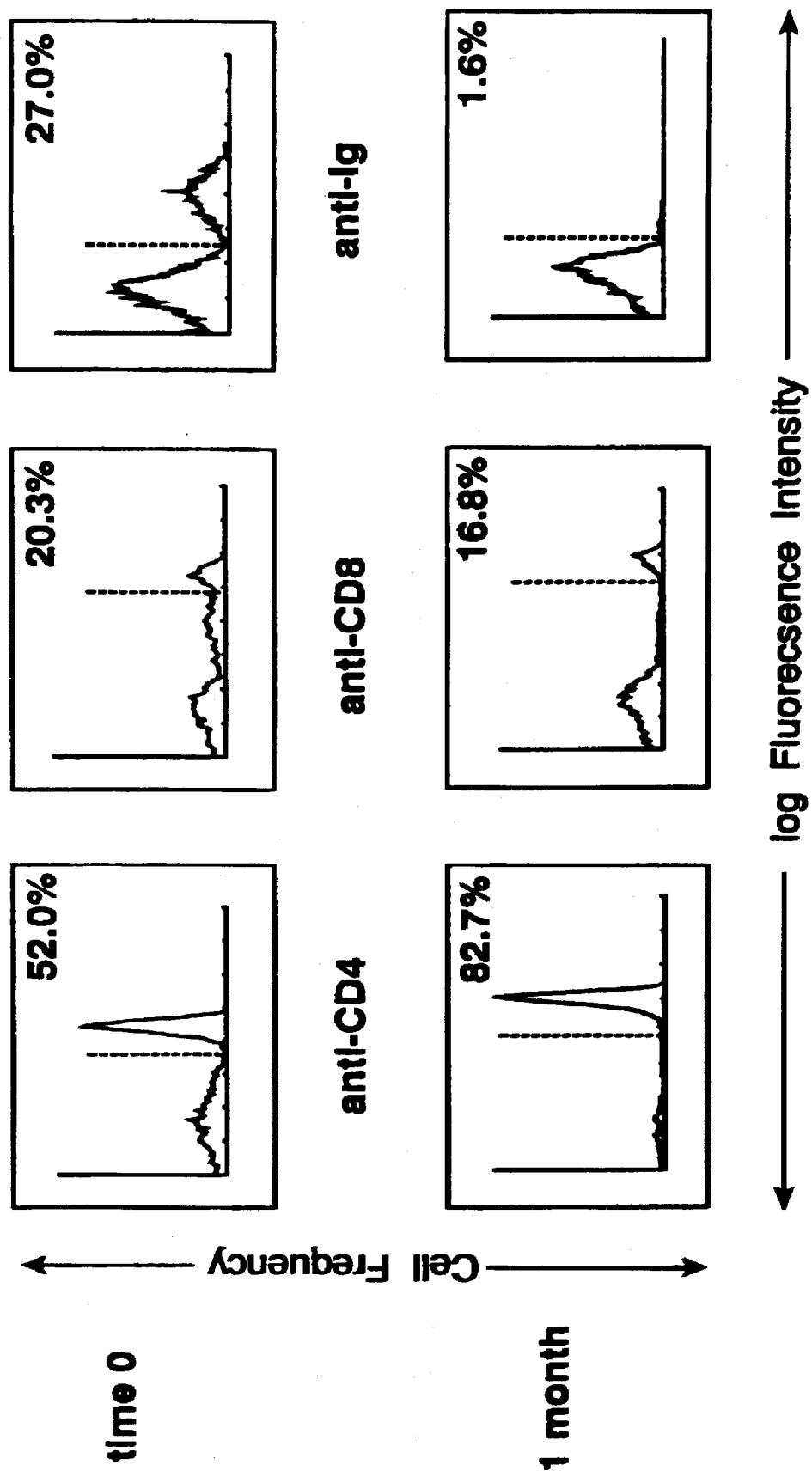
FIG. 2. Flow cytometric analyses of human peripheral blood cultures. Fresh human peripheral blood lymphocytes from healthy donors were isolated by density gradient separation on Hypaque ficoll. Long-term mononuclear cells were established as described in Materials and Methods. An aliquot of fresh cells was stained with FITC-labeled monoclonal antibodies specific for human CD4, CD8, and Ig, $10^6$ cells/sample. Long-term cultured cells were harvested for staining after 1 month. 5000 cells/sample were analyzed on an Epics Profile, depicted in each histogram. The Y-axis corresponds to the relative number of cells. The X-axis represents log of the fluorescence.

FIG. 2 depicts flow cytometric data of a representative long-term peripheral blood lymphocyte (PBL) culture at initiation and after 1 month in vitro. The results were very similar to the CBL cultures, in that the B cells initially present (27% of the cells) could not be detected after 1 month.

Cells were counted at various time points after initiation of culture to assess the total number of surviving cells. The biggest drop in T cell counts (32%), occurred within the first week of culture. At 4 weeks, an additional 13% were lost, and at 10 weeks after culture initiation 16% more cells were lost. It is likely that most of the cell loss during the first week represents the death of cells damaged during the purification procedure, since the percentage of cell loss declines to around 15% per month in the subsequent 8 weeks.

In both CBL and PBL cultures after 1 month or 3 months in vitro, the lymphocyte population consisted entirely of $CD3^+$ T cells (FIGS. 1 and 2). This was independent of whether modified Dexter conditions or Whitlock-Witte conditions with bFGF were applied. It is noteworthy that modified Whitlock-Witte culture conditions without addition of bFGF did not permit the formation of long-term cultures. B cells did not survive under any of the culture conditions employed. It was particularly interesting to note that the percentage of $CD4^+$ cells out of the total number of lymphocytes did not decrease even after 3 months in culture, as has been described with long-term interleukin-2-maintained cultures (Brunner et at., 1980, J. Immunol. 124:1627). $CD8^+$ T cells were also present at both time points. However, a subpopulation of weakly staining $CD8^+$ cells initially present in both CBL and PBL cultures did not persist in the long-term culture (FIGS. 1 and 2). The differences in the percentages of $CD8^+$ between the adult and the cord blood cultures at time 0 and after establishment of long-term cultures (FIGS. 1 and 2) could be due, in part, to the different proportions of the short-lived weakly staining $CD8^+$ population.

Since bFGF was needed for the maintenance of the Whitlock-Witte-type cultures, even though this cytokine has no direct effect on T cells (Burgess et al, 1989, Ann. Rev. Biochem. 58:575), we inferred that the adherent cell layer was dependent upon bFGF, and that the stromal-like cells in some manner sustained T cell growth. This hypothesis was supported by the fact that when T cells were removed from the adherent cells, and maintained in similar media with bFGF or with conditioned media from the original culture, over 80% died within 10 days. In contrast, T cells were not needed to sustain the adherent cells, since removal of the T cells did not alter the adherent cells' viability. Since Dexter culture conditions require the addition of high amounts of serum (20%) to the media, it was likely that there was enough bFGF (or other growth factors) in the serum to maintain viability of the adherent cells, making the addition of supplementary bFGF unnecessary.

Analysis of DNA synthesis by long-term T cells.

Although there was a slow decrease in the number of T cells over a period of 3 months, two sets of experiments were performed in order to assess whether some of these cells do proliferate in culture. First, the incorporation of $^3[H]$-thymidine by unstimulated T cells was measured at 2 week intervals. As a control for non-dividing cells we used mitomycin C-treated T cells, some of which were also stimulated with Con A (to control for the effect of mitomycin C). As shown in Table 1 below, thymidine incorporation by untreated T cells (medium) was very low, although it was slightly higher than mitomycin C-treated cells. This could be due to the fact that mitomycin C treatment results in a faster cell death rate, although the possibility that some cells in these long-term cultures are dividing cannot be eliminated.

TABLE 1

$^3[H]$-thymidine incorporation by resting long-term T cells (CPM)

| Treatment | Weeks in culture | | | | |
|---|---|---|---|---|---|
| | 0 | 2 | 4 | 6 | 8 |
| medium | 575 | 514 | 604 | 585 | 470 |
| mitomycin C | 471 | 419 | 470 | 480 | 448 |
| conA | 4,531 | ND | ND | 3,930 | ND |
| mitomycin C/con A | 549 | ND | ND | 484 | ND |

$7 \times 10^4$ cells per half area well were plated in medium containing 1.0 µCi $^3[H]$-thymidine for 12 hours. Con A and mitomycin C treatments are described in Materials and Methods. Results are expressed as mean of 3–6 cultures; standard deviation was always within 5 to 15% of the mean and has been omitted for simplicity.
ND = no data.

In a second set of experiments, the amount of newly synthesized DNA was determined by measuring the incorporation of BrdU using fluorescinated anti-BrdU antibodies as a probe. Again, no evidence of cell division resulting in DNA synthesis was observed (data not shown).

Peripheral blood T cells from long-term cultures can be activated with mitogens and respond to allogeneic stimulator cells in mixed lymphocyte reactions.

Figure 3:
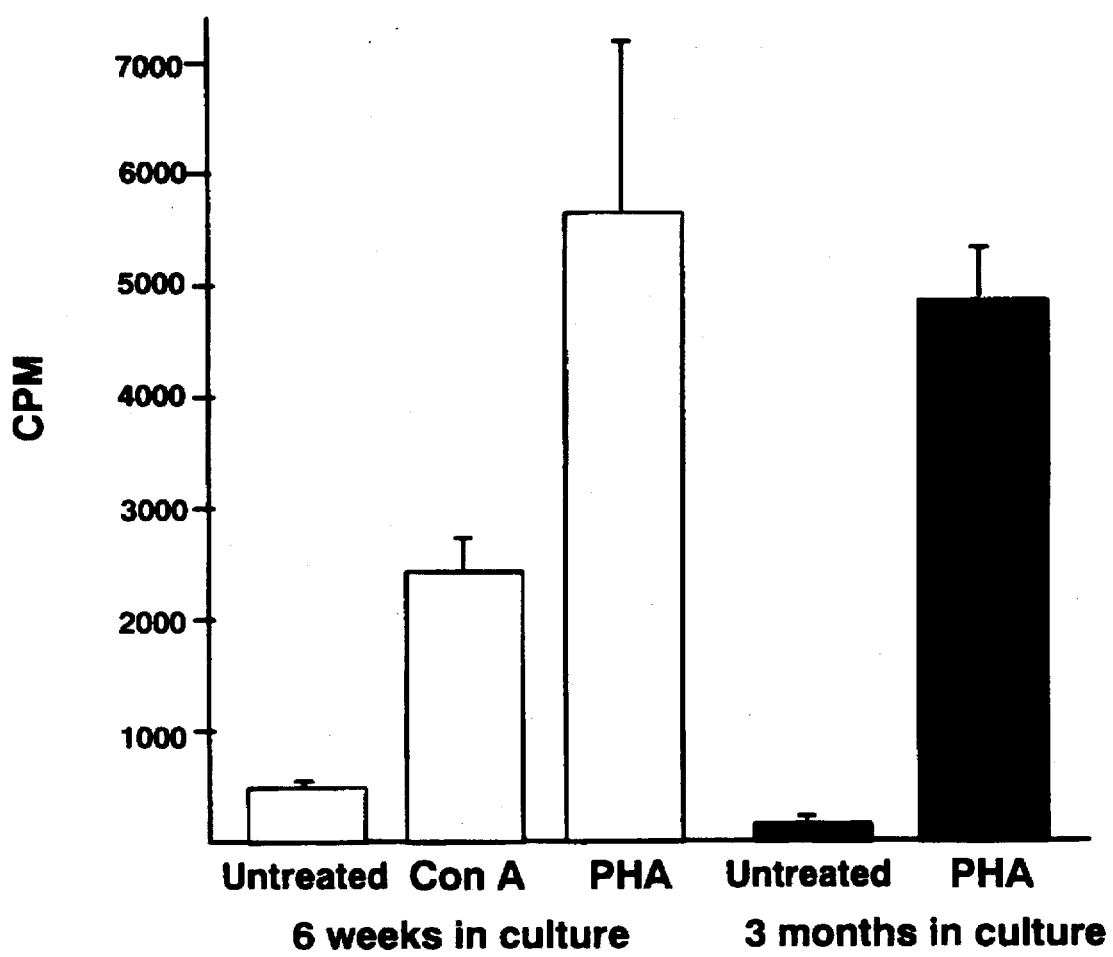
FIG. 3. The proliferative responses of long-term T cells to the mitogens phytohemagglutinin (PHA) and concanavalin A (Con A). Mitogenic responses were assayed by [$^3$H]-thymidine incorporation. T cells from long-term peripheral blood cultures were harvested after 6 weeks and 3 months, and plated in triplicate wells, with either PHA 4 µg/ml, Con A 4 µg/ml, or media only. Forty-eight hours later, cells were pulsed with [$^3$H]-thymidine for 12 h, then assayed for [$^3$H]-thymidine incorporation in a scintillation counter.
Figure 4:
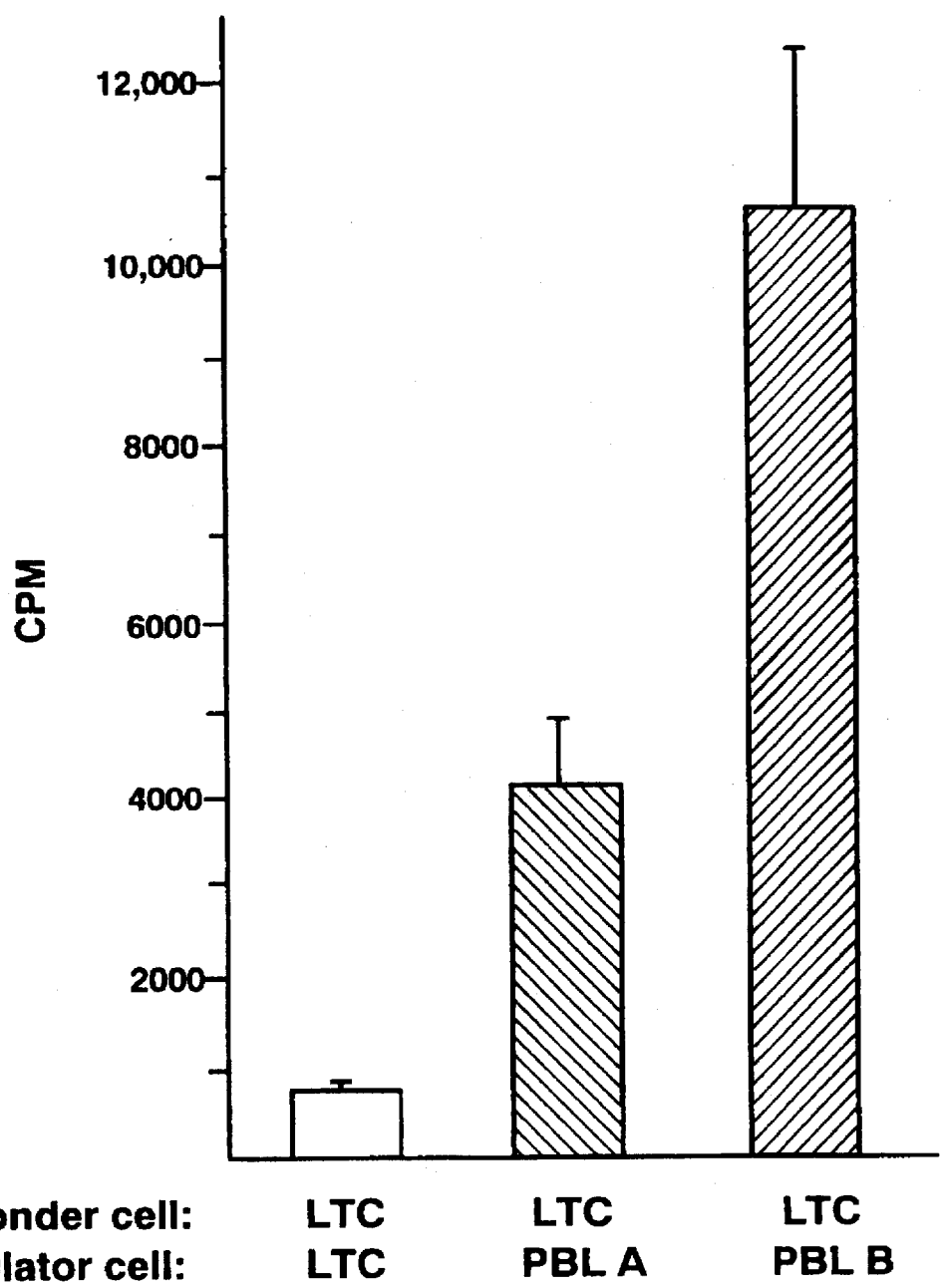
FIG. 4. The proliferative response of long-term T cells to allogeneic peripheral blood lymphocytes (PBL) as stimulators cells. Mixed lymphocyte responses were measured by [$^3$H]-thymidine incorporation. T cells from long-term PBL cultures were harvested after 2 months, and plated in triplicate wells with irradiated (1600 rad) PBL from 2 healthy donors (PBL A and PBL B). 72 h later, cells were pulsed with [$^3$H]-thymidine for 12 h, then assayed for [$^3$H]-thymidine incorporation in a scintillation counter.

The ability of PBL T cells harvested from long-term cultures to respond to the mitogens phytohemagglutinin (PHA) and concanavalin A (Con A), and to allogeneic cells after 6 weeks, 2 months, and 3 months in culture was tested in order to assess maintenance of their immune competence. T cell proliferation was measured by [$^3$H]-thymidine incorporation. As can be seen in FIG. 3, after 6 weeks in culture the T cells proliferated in response to both mitogens, although the response to PHA was somewhat increased over the primary T cell response. After 3 months in culture the T cell response to PHA held steady. Allogeneic responses were measured at 2 months against two different stimulator peripheral blood cell populations. As depicted in FIG. 4, the long-term T cells responded against both allogeneic donor cells as measured by [$^3$H]-thymidine incorporation.

The adherent cell population from the long-term cultures is composed of endothelial-like cells with varied morphology.

Figure 5A:
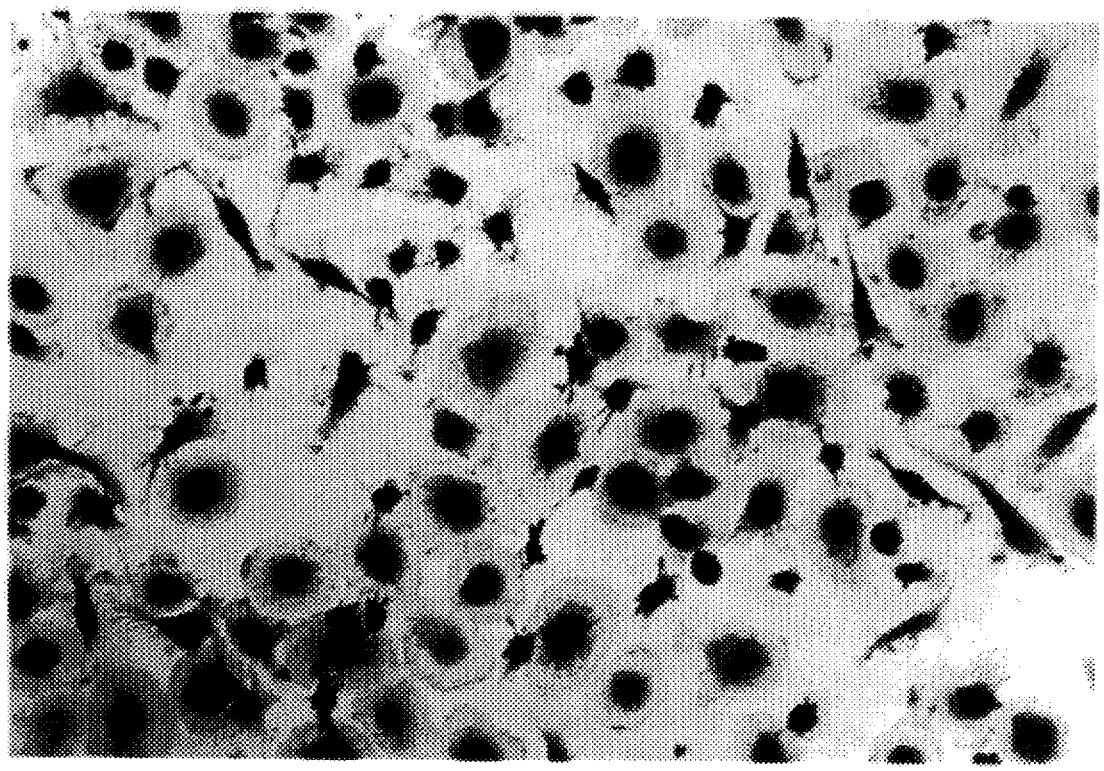
FIGS. 5A and 5B. Hematoxylin/eosin staining of the peripheral blood-derived monolayer cells. (A) 200X and (B) 400X magnification. Stromal-like cells have varied morphology, some spindle-shaped, others more rounded. Lymphocytes can occasionally be detected (much smaller cells).
Figure 5B:
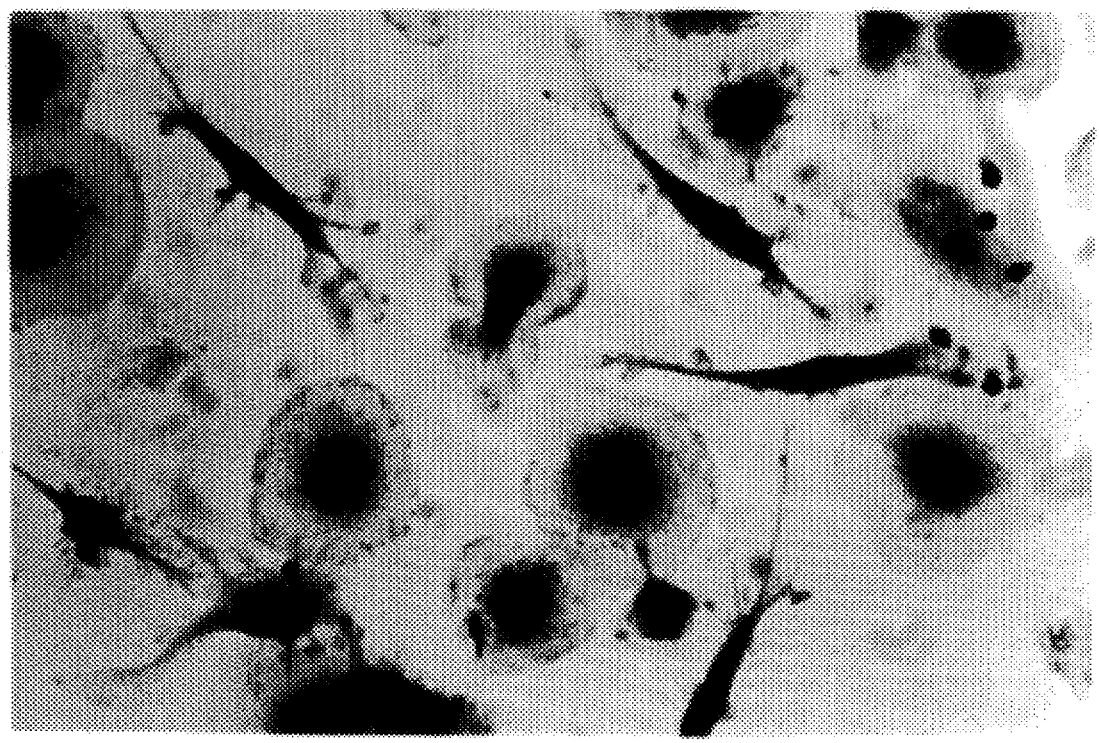

The phenotype of the supportive adherent cell layer was characterized by immunohistochemistry using a battery of monoclonal antibodies specific for the cell surface markers listed in Table 2. Although all of the adherent cells had an identical antibody staining profile, morphologically, the cells could be classified into at least two distinct types. Usually, about half the cells had a spindle-shaped morphology, and the other half had a macrophage like morphology (FIG. 5). The cells were large, and stained positively for fibronectin, laminin, and vimentin. Because of their morphology, and because the cells were derived from peripheral blood or umbilical cord blood, it is suspected that their origin is of the macrophage or endothelial cell lineages, although fibroblast, dendritic cell, smooth muscle cell, and the like lineages are also a possibility. Since the adherent cells did not express either the leukocyte common antigen (CD45) or the macrophage marker MO-2 (CD14), and because macrophages are not known to be dependent upon bFGF, it is most likely that the cells were not macrophages. The cells were also negative for muscle-specific actin, indicating that they are not of smooth muscle origin. The fact that the adherent cells were responsive to bFGF and that they expressed PECAM-1 (platelet-endothelial cell adhesion molecule-1, CD31) strongly suggested that they are of endothelial origin (Burgess et al, 1989, Ann. Rev. Biochem. 58:575; Springer, 1994, Cell 76:301). Moreover, all adherent cells, independent of their morphology, stained very strongly with anti-E-selectin (ELAM-1, CD62E) antibodies (Table 2). E-selectin is a marker for activated endothelial cells and cannot be detected by staining on resting endothelial cells (Springer, 1994, Cell 76:301). All adherent cells also expressed HLA DR antigens which, is also characteristic of activated endothelial cells. The cells, however, were negative for Factor VIII-related antigen, another common endothelial cell marker. We thus refer to the cells as endothelial-like.

TABLE 2

Monoclonal antibody staining profile of the peripheral blood-derived monolayer

| Antigen | Main Cellular Expression | Staining |
| --- | --- | --- |
| HLA ABC (MHC Class I) | All cell types | (+) |
| HLA DR (MHC Class II) | Macrophages, B cells, dendritic, endothelial cells | (+) |
| CD45 (Leukocyte Common Antigen) | Pan-leukocyte | (−) |
| CD14 (MO-2) | Macrophages, Monocytes | (−) |
| CD31 (PBCAM-1) | Platelets, Endothelial cells | (+) |
| E-selectin (ELAM-1, CD62E) | Activated endothelial cells | (+) |

TABLE 2-continued

Monoclonal antibody staining profile of the peripheral blood-derived monolayer

| Antigen | Main Cellular Expression | Staining |
| --- | --- | --- |
| CD34 | Stem cells, Endothelial cells | (+/−) |
| Factor VIII | Endothelial cells | (−) |
| Actin | Muscle-specific | (−) |
| Fibronectin | Extracellular matrix | (+) |
| Laminin | Extracellular matrix | (+) |
| Vimentin | Intermediate filament | (+) |

Peripheral blood-derived monolayer cells were analyzed by immunohistochemical staining of various cell surface markers. Cells were fixed, then stained with monoclonal antibodies specific for each marker using immunoperoxidase staining. Cells were scored +/− under light microscopy.

It is noteworthy that these endothelial-like cells have an antibody staining profile similar to that of certain Kaposi sarcoma (KS) cell lines (Kamada et al., 1992, Cancer 70:861; Kostianovsky et al., 1992, Ultrastructural Pathol. 16:629; Regezi et al., 1993, Amer. J. Pathol. 143:240), which also stain positive for some endothelial markers. The origin of KS cells has been subject to some controversy. However, it is now generally accepted that they are of endothelial origin (Regezi et al., 1993, Amer. J. Pathol. 143:240; O'Connell and Rudman, 1993, J. Invest. Dermatol. 100:742). Like some of the adherent cells described here, KS cell lines also have spindle-like morphology (Regezi et al., 1993, Amer. J. Pathol. 143:240; Ensoli et al., 1991, Hematol. Oncol. Clin. N. Amer. 5:281; Barillari et al., 1992, J. Immunol. 149:3727; Bisceglia et al., 1992, Cancer 69:793; Kaaya et al., 1992, Eur. J. Cancer 28A:1890), and they are also very responsive to bFGF (Barillari et al., 1992, J. Immunol. 149:3727; Ensoli et al., 1989, Science 243:223; Schulze-Osthoff et al., 1990, J. Invest. Dermatol. 95:238).

Because it has been reported that KS cell lines proliferate in response to PHA-activated T cell-conditioned media (Barillari et al., 1992, J. Immunol. 149:3727), PHA was added to some of the long-term cultures. Indeed, activation of the T cells by PHA appeared to stimulate growth of the adherent cell layer, most likely by factors secreted by the activated T cells. The adherent cells approximately doubled in number within 5 days of addition of PHA (data not shown). Interestingly, when the PHA was washed away 24–48 hours after addition to the cultures, the stimulated T cells appeared to proliferate for several days, and then reverted back to a resting morphology. This observation is in contrast to the characteristic cell death that follows PHA stimulation of purified T cells.

Long-term cultured T cells can be efficiently infected with a retroviral vector and express an exogenous gene.

Figure 6A:
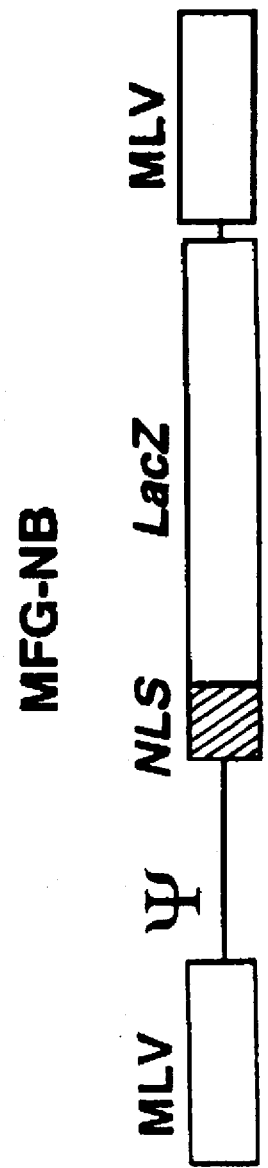
FIGS. 6A through 6D. Long-term peripheral blood (PBL) T cells infected with the retroviral vector MFG-NB. (A) The retroviral vector MFG-NB is an MLV-based vector containing the lacZ gene fused to a nuclear localization sequence from simian virus 40. It is expressed by the viral LTR. Fresh PBL and T cells from 2 month old cultures were infected with MFG-NB as described in Materials and Methods. Two days later, cells were fixed and stained with X-gal. (B) Infected 2 month-old T cells; (C) infected fresh PBL; (D) uninfected controls.
Figure 6B:
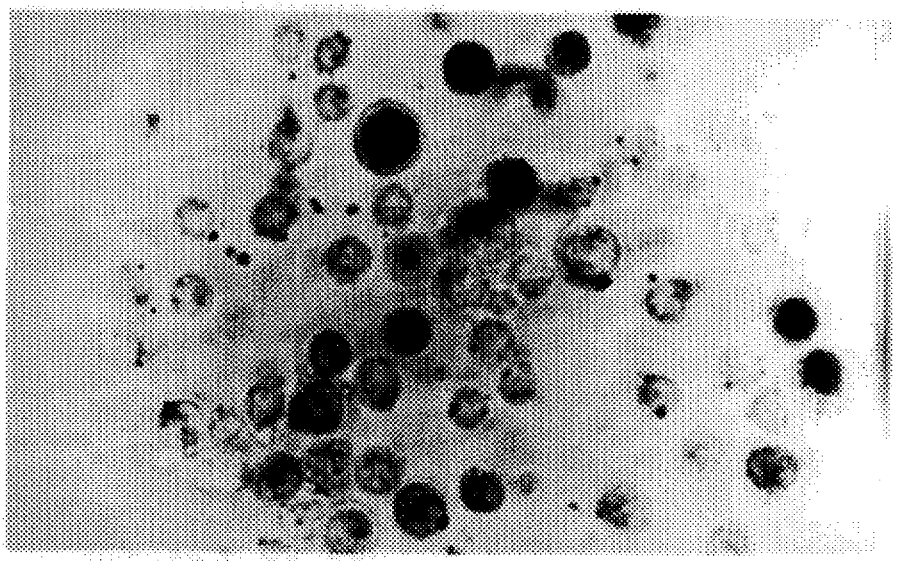
Figure 6C:
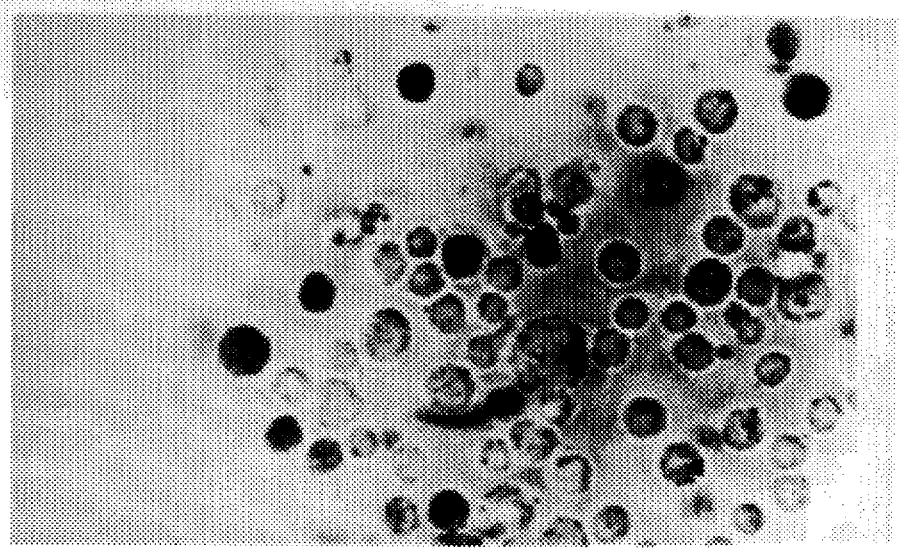
Figure 6D:
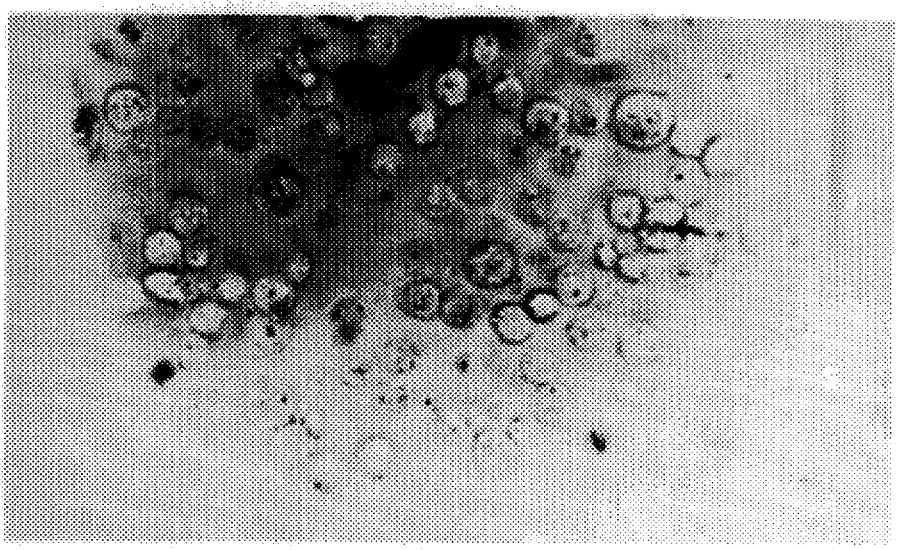

Since the T cells harvested from the long-term cultures were immune competent, they could be of potential use as target cells for gene therapy protocols. To test whether the cells could be efficiently transduced with a retroviral vector containing the lacZ gene with a nuclear localization signal as a marker gene, PBL T cells from 2 month-old cultures were infected, using a protocol originally designed for the infection of fresh primary T cells (see copending U.S. patent application Se. rNo. 08/302,232 by Dougherty et al., and International Patent Publication WO 95/07358, Mar. 16, 1995, by Dougherty et al.) and (Kuo et al., 1993, Blood 82:845). MMG producer cells packaged the Moloney murine leukemia virus-based vector MFG-NB (Ferry et al., 1991, Proc. Natl. Acad. Sci. USA 88:8377) with amphotropic envelope proteins from gibbon-ape leukemia virus (FIG. 6A). The vector virus produced by these cells can infect human cells. Long-term T cells were stimulated overnight with PHA, then washed and cocultivated with lethally-irradiated MMG cells that produced vector virus at a titer of $2 \times 10^7$ CFU/ml, in the presence of interleukin-2 and polybrene for 24 h. The target T cells were then harvested and cultured for 48 h to allow the cells time to express the exogenous lacZ gene. Fresh peripheral blood T cells were simultaneously infected as a control. To determine the percentage of cells that expressed the exogenous gene, the target cells were fixed and stained with X-gal, and blue cells were counted. As can be seen in FIG. 6, on average, 20–30% of the 2 month-cultured T cells expressed lacZ after cocultivation (FIG. 6B), compared to 21–28% of the fresh peripheral blood T cells (FIG. 6C) and uninfected controls (FIG. 6D). This indicates that the long-term cultured T cells might be suitable for certain gene therapy applications.

Discussion

The data presented here show that bFGF-responsive adherent cells with surface markers closely resembling those of activated endothelial cells can be cultured from the peripheral blood and can support the growth of primary T lymphocytes in vitro for several months. The T cell population retains the original ratio of CD4$^+$ cells to CD8$^+$ cells. The resting T cells in long-term culture on the adherent layer do not proliferate at a high rate if at all. It is probable that the adherent cells secrete an as yet unknown factor(s) that maintains the T cells in a quiescent state. The resting T cells can be activated to proliferate in response to mitogens, such as PHA and Con A, or antigens, such as allogeneic cells, even 3 months after initiation of the cultures (FIG. 3).

The phenotype of the endothelial-like adherent cells resembles that described for Kaposi sarcoma (KS) cells. All of the surface markers found on the stromal-like monolayer have been described for various isolates of KS cells, including the fact that some are negative for Factor VIII-related antigen, a common endothelial cell marker sometimes absent from KS cells (Kamada et al., 1992, Cancer 70:861; Kostianovsky et al., 1992, Ultrastructural Pathol. 16:629; Regezi et al., 1993, Amer. J. Pathol. 143:240). Although the origin of KS cells is a matter of uncertainty, it is generally believed that they are of endothelial origin (Kostianovsky et al., 1992, Ultrastructural Pathok 16:629; Regezi et al., 1993, Amer. J. Pathol. I43:240; O'Connell and Rudman, 1993, J. Invest. Dermatol. 100:742). Studies using bFGF and PHA-stimulated T cell-conditioned media (CM) indicated that KS cells proliferate in response to bFGF and other cytokines present in the CM (Barillari et al., 1992, J. Immunol. 149:3727; Ensoli et al., 1989, Science 243:223; Schulze-Osthoff et al., 1990, J. Invest. Dermatol. 95:238). Similar results were obtained for the stromal-like monolayer cells (data not shown). It is therefore tempting to speculate that these stromal-like cells might be the normal counterpart of the KS cells.

The development of a system in which primary CD4$^+$ and CD8$^+$ T lymphocytes can be maintained in vitro for long periods of time without the need for activation suggests a number of applications. The most obvious use would be for studies on T lymphocyte biology. Currently, the majority of studies concerning T cell activation are performed on either T cell hybridomas or T cell lines. Primary T cells must be maintained with IL-2 to survive in vitro, and the effects of IL-2 are likely to obscure other signaling molecules and lead to artificial functional activity and phenotype. Using the present system for long term culturing of resting T cells, the effects of various signaling molecules on the induction of very late antigens could be studied, independent of the effects of exogenous IL-2. Similarly, the effects of molecules that might induce apoptosis of T lymphocytes at various time points post-signaling can also be readily assessed in the present a system.

The ability to culture resting T cells for long periods has diagnostic implications as well. T cells can be maintained in culture and evaluated for functional activity, e.g., responses to various antigens.

A second potential application of the long-term T lymphocyte cultures is for studying the interaction of viruses, in particular HIV, with T lymphocytes. Since in this system T cells can be activated with mitogens without induction of massive cell death, the role of various cellular genes such as NF-KB, TNF-$\alpha$, and other cytokines on the viral life cycle can be readily assessed. This system is also useful for resolving the controversial issue of latency of HIV infection, since the infected cells can be maintained on the adherent cell layer for long periods of time. In addition, HIV infection of non-dividing cells can be directly assessed in this system. Furthermore, various agents that might be required for, or conversely, block infection could be screened using this in vitro system.

A third use of these primary T cell cultures is in somatic cell gene therapy. FIG. 6 demonstrates that the long-term cultured cells could be efficiently infected with a retroviral vector. Although gene therapy applications may employ fresh primary T cells, it might not always be possible to obtain enough fresh PBL, especially from newborns. A particular use might be in HIV gene therapy for neonates, once the technology for intracellular immunization protocols has been developed (Malim et al., 1992, J. Exp. Med. 176:1197; Sarver et al., 1990, Science 247:1222; Joshi et al., 1991, J. Virol. 65:5524). The umbilical cord blood from babies born of HIV-positive mothers could be cultured until it is known for certain whether the babies are also infected with HIV. The T cells that arise in these cultures would be amenable to such gene therapy approaches.

The long term T cell cultures can also be used to replenish T cells in individuals treated with lymphocyte and bone-marrow toxic therapies, e.g., chemotherapy or radiation to ablate lymphomas, leukemias, and similar blood cell cancers (but not T cell lymphomas). The long-term cultured T cells, if necessary purified away from cancer cells, could be reintroduced along with bone marrow to more rapidly and naturally reconstitute the immune system.

This invention may be embodied in other forms or carried out in other ways without departing from the spirit or essential characteristics thereof. The present disclosure is therefore to be considered as in all respects illustrative and not restrictive, the scope of the invention being indicated by the appended Claims, and all changes which come within the meaning and range of equivalency are intended to be embraced therein.

Various references are cited throughout this specification, each of which is incorporated herein by reference in its entirety.

What is claimed is:

1. A composition for the long-term culture of resting T lymphocytes, comprising cell culture medium, resting T lymphocytes, and a layer of endothelial-like adherent blood monocytes, wherein the culture medium comprises an adherent blood monocyte growth factor.

2. The composition of claim 1, wherein the endothelial-like adherent blood monocytes are derived from peripheral blood.

3. The composition of claim 1, wherein the endothelial-like adherent blood monocytes are derived from umbilical cord blood.

4. The composition of claim 1, wherein the endothelial-like adherent blood monocytes are human.

5. The composition of claim 1, wherein the T lymphocytes are peripheral blood T lymphocytes.

6. The composition of claim 1, wherein the T lymphocytes are umbilical cord blood T lymphocytes.

7. The composition of claim 1, wherein the T lymphocytes are human T lymphocytes.

8. The composition of claim 1, wherein the adherent blood monocyte growth factor is a high concentration of serum.

9. The composition according to claim 8, wherein the high concentration of serum is greater than 15% of culture medium.

10. The composition of claim 1, wherein the adherent blood monocyte growth factor is basic fibroblast growth factor present in an amount effective to maintain the adherent blood monocytes.

* * * * *